United States Patent [19]
Hooven

[11] Patent Number: 5,518,164
[45] Date of Patent: May 21, 1996

[54] ENDOSCOPIC SURGICAL SYSTEM WITH SENSING MEANS

[75] Inventor: Michael D. Hooven, Cincinnati, Ohio

[73] Assignee: Ethicon, Inc., Somerville, N.J.

[21] Appl. No.: 451,856

[22] Filed: May 26, 1995

Related U.S. Application Data

[62] Division of Ser. No. 323,467, Oct. 14, 1994, which is a continuation of Ser. No. 991,619, Dec. 14, 1992, Pat. No. 5,383,880, which is a continuation-in-part of Ser. No. 822,478, Jan. 17, 1992, abandoned.

[51] Int. Cl.⁶ .................................................. A61B 17/068
[52] U.S. Cl. ...................... 227/1.005; 227/19; 227/180.1; 227/126.1; 606/142; 600/104
[58] Field of Search .................................... 227/175, 176, 227/180, 178, 19; 128/4; 606/142

[56] References Cited

U.S. PATENT DOCUMENTS

| | | | |
|---|---|---|---|
| 3,662,939 | 5/1972 | Bryan | 227/19 |
| 4,402,311 | 9/1983 | Hattori . | |
| 4,403,890 | 9/1983 | Miyanagi et al. | 405/184 |
| 4,487,270 | 12/1984 | Huber | 173/12 |
| 4,494,549 | 1/1985 | Sakai . | |
| 4,534,420 | 8/1985 | Goldelius | 173/12 |
| 4,606,343 | 8/1986 | Conta . | |
| 4,674,515 | 6/1987 | Andou . | |
| 4,705,038 | 11/1987 | Sjostrom . | |
| 4,732,156 | 3/1988 | Nakamura . | |
| 4,742,815 | 5/1988 | Ninan . | |
| 4,756,309 | 7/1988 | Sachse . | |
| 4,815,469 | 3/1989 | Cohen . | |
| 4,890,602 | 1/1990 | Hake | 128/4 |
| 4,893,613 | 1/1990 | Hake | 128/4 |
| 4,907,973 | 3/1990 | Hon . | |
| 4,928,699 | 5/1990 | Sassi . | |
| 4,955,882 | 9/1990 | Hakky . | |
| 4,982,726 | 1/1991 | Taira | 128/4 |
| 5,077,506 | 12/1991 | Krause . | |
| 5,171,247 | 12/1992 | Hughett et al. | 606/142 |
| 5,171,251 | 12/1992 | Bregen et al. | 606/151 |
| 5,197,649 | 3/1993 | Bessler et al. . | |
| 5,207,691 | 5/1993 | Nardella . | |
| 5,258,007 | 11/1993 | Spetzler et al. . | |

FOREIGN PATENT DOCUMENTS

| | | |
|---|---|---|
| 0116220A1 | 8/1984 | European Pat. Off. . |
| 0121474A3 | 10/1984 | European Pat. Off. . |
| 0399701 | 11/1990 | European Pat. Off. . |
| 0514139A3 | 11/1992 | European Pat. Off. . |
| 2044108 | 10/1980 | United Kingdom . |
| 2180455 | 4/1987 | United Kingdom . |
| WO82/03545 | 10/1982 | WIPO . |
| WO83/00992 | 3/1983 | WIPO . |
| WO90/05491 | 5/1990 | WIPO . |
| WO92/16141 | 10/1992 | WIPO . |

*Primary Examiner*—Scott A. Smith
*Attorney, Agent, or Firm*—Paul A. Coletti

[57] ABSTRACT

An endoscopic surgical system which includes an instrument for carrying out a step in the procedure. The instrument is power operated and the system includes sensing elements to control the operation of the instrument.

9 Claims, 15 Drawing Sheets

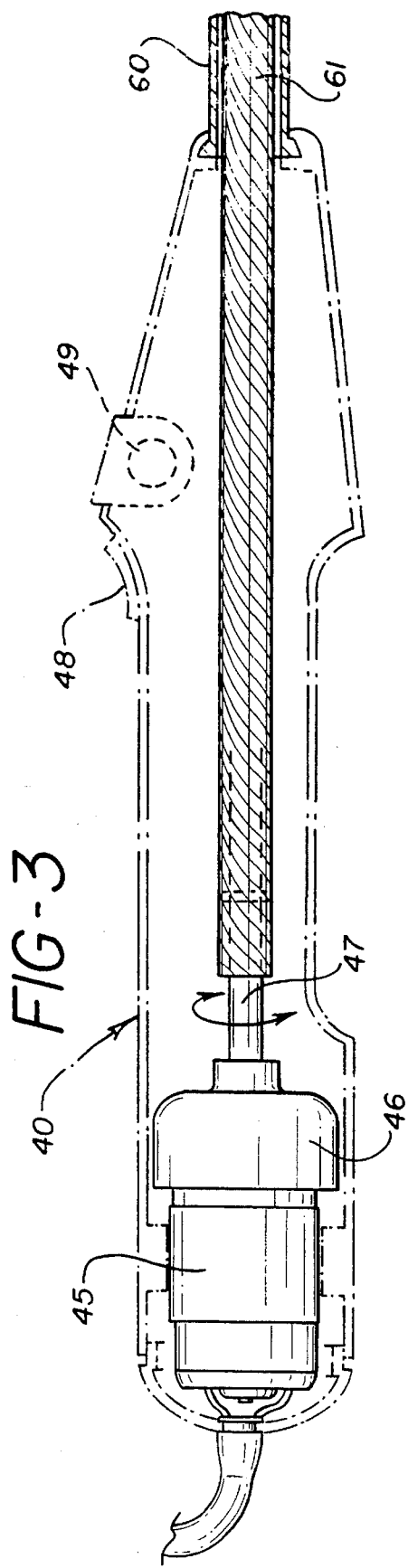
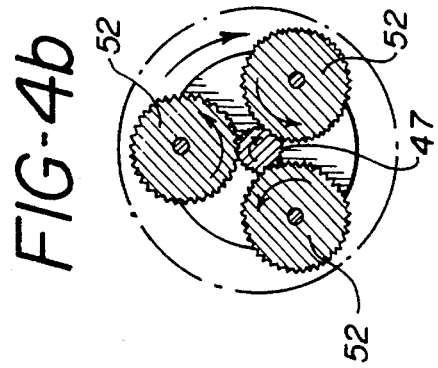
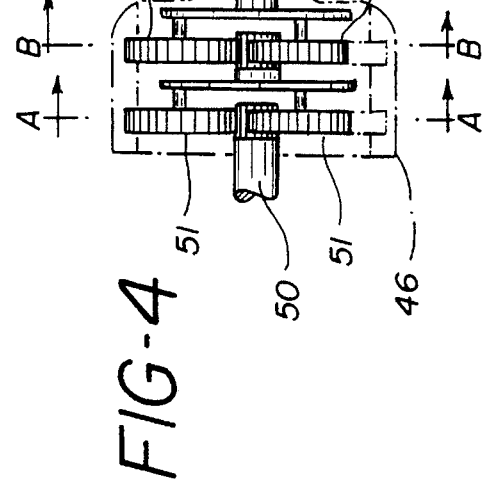

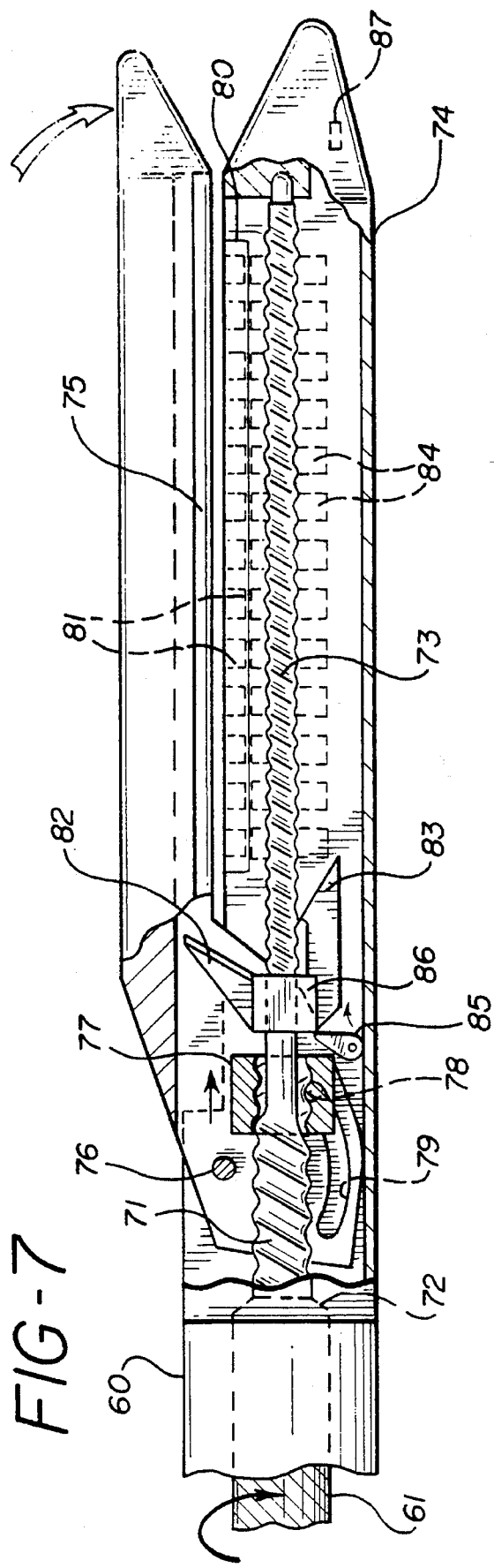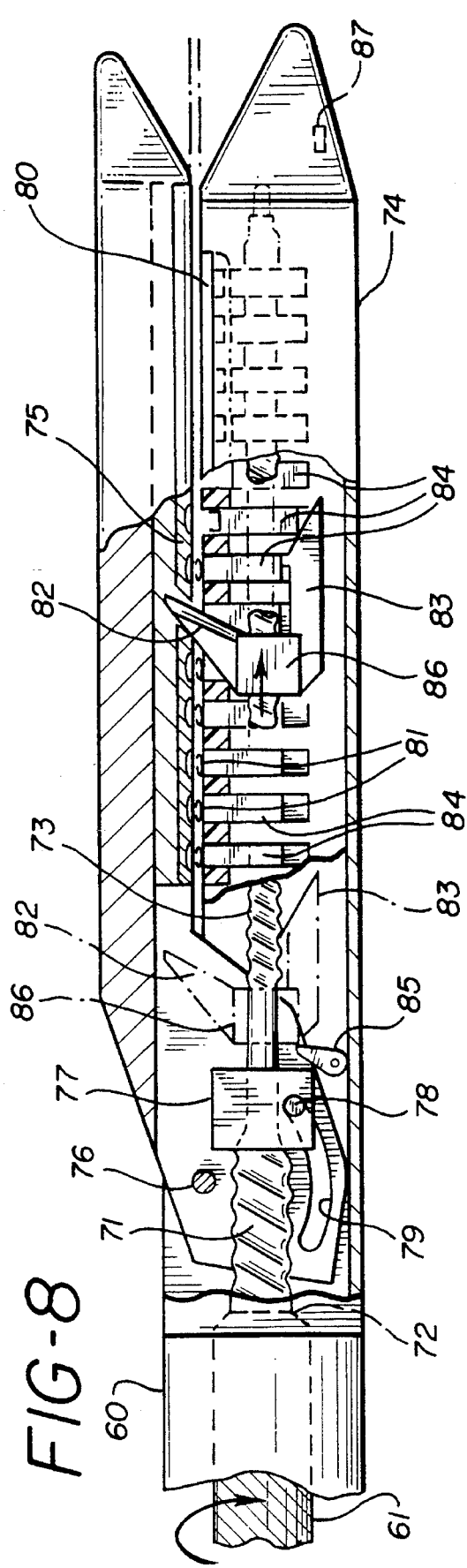

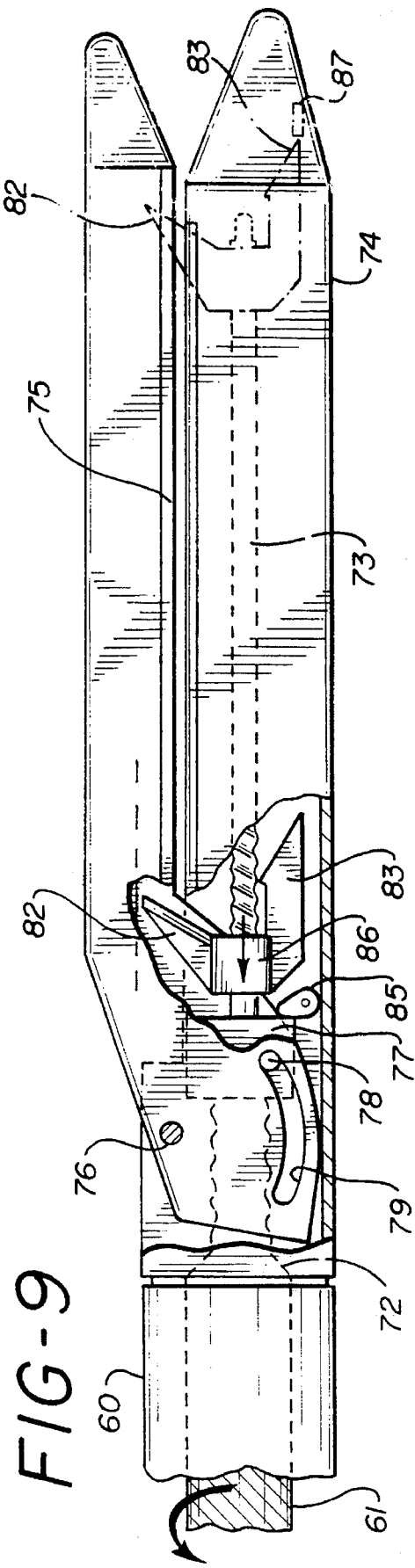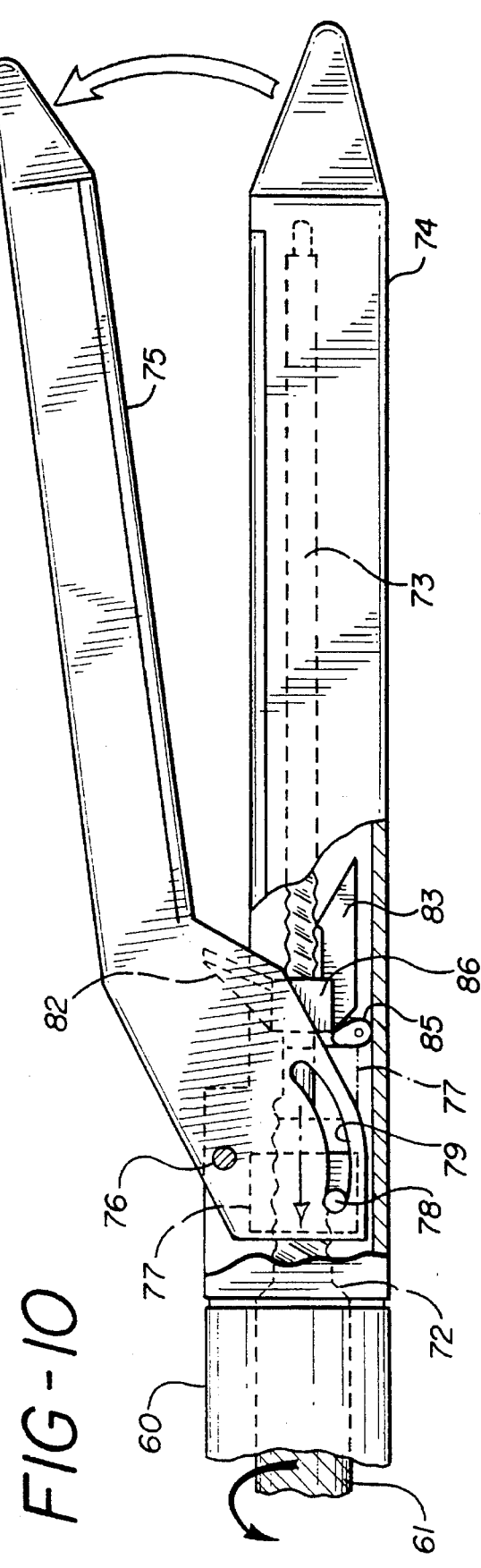

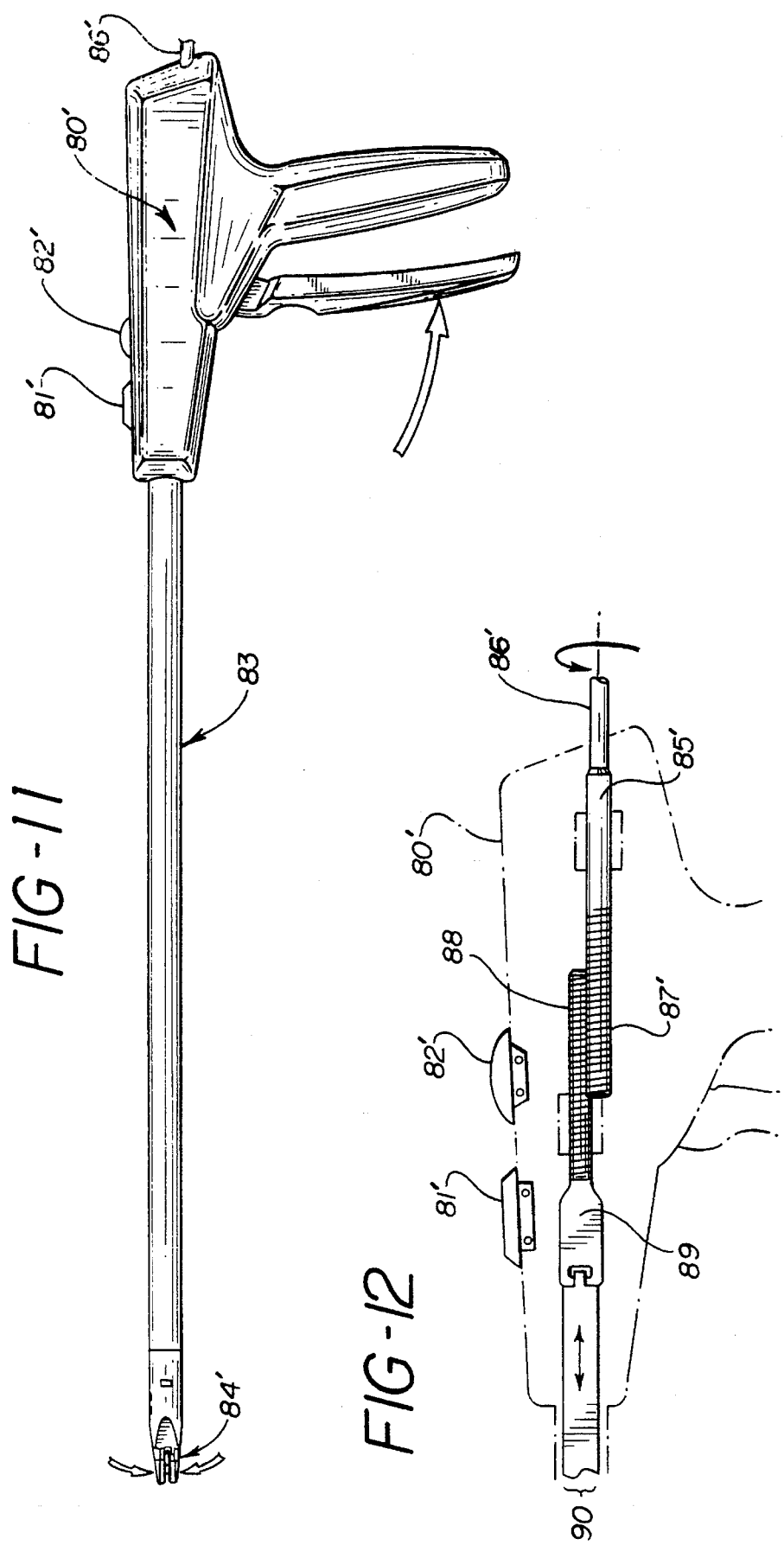

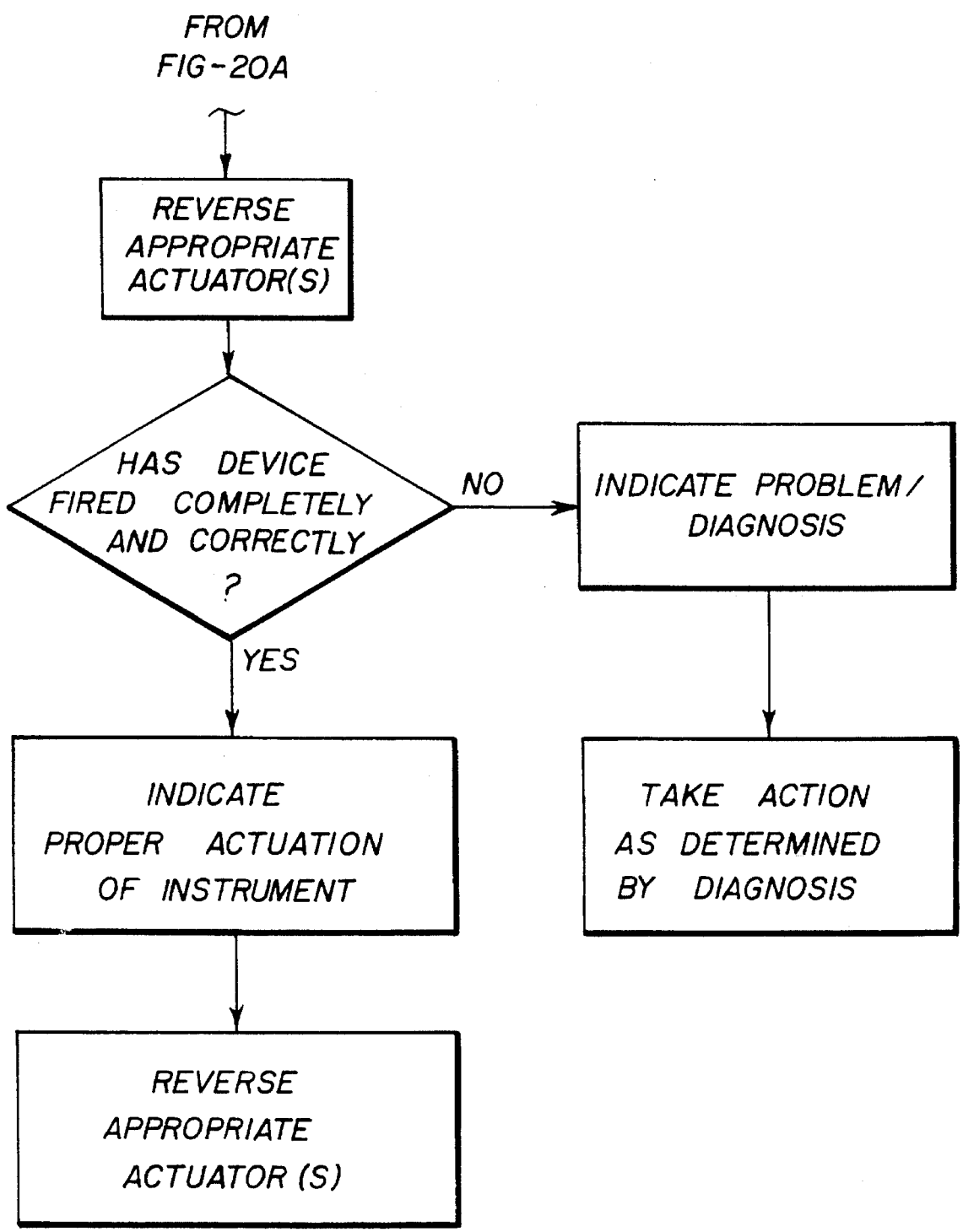

ENDOSCOPIC SURGICAL SYSTEM WITH SENSING MEANS

RELATED PATENT APPLICATION

This is a division of application Ser. No. 08/323,467, filed Oct. 14, 1994, pending, which is a continuation of Ser. No. 07/991,619, filed Dec. 16, 1992, now U.S. Pat. No. 5,383,880, which is a continuation-in-part of Ser. No. 07/822,478, filed Jan. 17, 1992, now abandoned, which is hereby incorporated by reference.

FILED OF THE INVENTION

This invention relates to a system for use in endoscopic procedures. More specifically, this invention relates to a system which will automatically sense physical properties of the tissue on which the procedure is being conducted and/or certain parameters of an endoscopic surgical instrument.

BACKGROUND OF THE INVENTION

Endoscopic surgery has been gaining wide acceptance as an improved and cost effective technique for conducting certain surgical procedures. In endoscopic surgery, a trocar, which is a pointed piercing device, is sent into the body with a cannula placed around the trocar. After the trocar accomplishes piercing of the abdominal walls, it is removed and the cannula remains in the body. Through this cannula, endoscopic procedures are possible. Often multiple openings are produced in the body with a trocar so that an endoscopic instrument may be placed in one cannula, appropriate viewing mechanisms placed in another cannula and fiber optics for illuminating the surgical field placed in yet another cannula. Generally, these endoscopic procedures take place under insufflation. As more is learned about endoscopic procedures and more instruments developed, the type of procedures that may be performed endoscopically will increase. Presently, typical procedures are gall bladder removal, tissue repair and various sterilization procedures.

Broadly, the instruments used in surgery can be classified into two broad classes. One class is manipulation devices; that is, devices which will grasp tissue, position tissue, irrigate, apply suction, and the like. The second class may be termed active devices. Generally, these devices either cut or staple tissue and some devices may combine these actions. Examples of such devices are electrosurgery instruments, ultrasonic instruments, lasers, circular stapling instruments, linear stapling instruments, ligating and cutting instruments and the like.

While endoscopic surgical procedures have substantial benefits to the patient, they do present certain problems to the surgeon conducting the procedure. For example, because the active part of the instrument is further removed from the manipulative part of the instrument, any slight movement of that manipulative part is magnified when it reaches the active part. Hence, when placing and forming a staple in tissue, the hand of the surgeon must be a lot steadier during the endoscopic procedure than if that same procedure was done during standard open surgery. Another difficulty arises because the surgeon, conducting the procedure, cannot see the field in which he is operating in a direct manner but is watching that field on an appropriate video display and manipulating the instrument based on what he sees on that video display. Hence, in designing endoscopic surgical instruments, considerable effort is made to reduce the force required in order to operate the instrument and allow the surgeon to have greater control over the instrument. Also, from an engineering standpoint, considerable design engineering is required to permit function of the active portion of the instrument given the physical limits of force and stroke of the surgeon's hand.

Another problem, particular to endoscopic procedures, is that the surgeon can no longer feel tissue with his hands to determine thickness, consistency, texture, etc.

It should also be pointed out, that for medical reasons it is often desirable to make endoscopic instruments disposable. A major reason for this is that small, intricate, reusable instruments are difficult to sterilize and, if you can make the instrument disposable these sterilization problems are eliminated. However, making the instrument disposable will often increase the cost of the instrument and this cost must be balanced with the medical advantage. Another problem with endoscopic instruments is their access limitations; that is, the ability to manipulate the head of the instrument after it has been placed in the cannula is difficult and the scope of movement is limited.

SUMMARY OF THE INVENTION

The endoscopic surgical system of the present invention provides a system allowing for a high degree of control in the manipulation of the active part or business head of an endoscopic instrument. Furthermore, my new system may provide greater access for the head of an endoscopic instrument during the surgical procedure. My new endoscopic system allows for greater forces to be applied at the head of the instrument while maintaining that head under stable control during the surgical procedure. My new endoscopic system may be disposable and even when disposable, in certain designs, may provide considerable reduction in cost. My new system allows the surgeon to expend less energy during the surgical procedure thus providing for improved manipulation and control of the instrument during the procedure. My new endoscopic system provides sensing feedback to the surgeon to compensate for the loss of tactile feedback. In certain designs of my new endoscopic system, the surgeon is provided with considerable knowledge regarding the instrument. For example, the surgeon may be informed as to the position of the instrument in the procedure, the operation of the instrument; i.e., whether it is in a position to be activated and activated correctly and the like.

In its broadest sense, my new endoscopic system comprises an instrument which is to be used in conducting a step in an endoscopic procedure. Connected to that instrument is suitable power means which will operate the active or business head of the instrument to conduct a desired step in the procedure. The instrument also includes a sensing means which controls and/or monitors the operation of the instrument while conducting the desired step in the procedure and provides feedback information to the surgeon. According to the present invention, there is provided an endoscopic instrument which has a head portion for carrying out a step in an endoscopic procedure. The step may be ligating, stapling, cutting, manipulation of the tissue etc. or combinations of these steps. Connected to this head portion is a shaft. The instrument includes means for applying energy to the head portion either by or through the shaft. In preferred embodiments of the present invention, the shaft is encased in a housing and a motion is provided to the shaft; i.e., rotation, longitudinal movement, etc. Means are disposed in the head of the instrument, to translate the motion of the shaft into a suitable force and/or motion in the head to carry out a desired step in the procedure; i.e., to set and form staples or to ligate a vessel or to sever tissue and so forth. Also, disposed in the head portion is a sensing means which measures the energy, force, or the motion of the head portion. In some instances, the sensing means may measure one or more physical parameters of the tissue on which it is to work or of the surrounding tissue. Inter-connected with that sensing means is a means which controls the energy, force and/or the motion of that head portion.

The present invention will be more readily understood and described in the attached description of the drawings taken in conjunction with the description of the invention.

BRIEF DESCRIPTION OF THE DRAWINGS

FIG. 3 is a longitudinal cross-sectional view of the handle portion of one embodiment of an endoscopic stapling and cutting system of the present invention;

FIG. 4 is a detail of the gear reduction assembly.

FIG. 4a is a cross-sectional view taken along line A— A of FIG. 4;

FIG. 4b is a cross-sectional view taken along line B— B of FIG. 4;

FIG. 7 is an enlarged longitudinal cross-sectional view of the head of the system depicted in FIG. 6 with the head in a closed position;

FIG. 8 is an enlarged longitudinal cross-sectional view of the head of the system depicted in FIG. 6 with the head in the position of firing staples;

FIG. 9 is an enlarged longitudinal cross-sectional view of the head of the system of FIG. 6 with the head in the closed position after firing the staples;

FIG. 10 is an enlarged longitudinal cross-sectional view of the head of the system depicted in FIG. 6 with the head in the open position after the staples have been fired;

FIG. 11 is a perspective view of another embodiment of an endoscopic system of the present invention useful in placing ligating clips;

FIG. 12 is a longitudinal cross-sectional view of the handle of the instrument depicted in FIG. 11;

FIG. 20 comprising FIG. 20A and 28B is a simplified flow diagram of one possible flow for the control logic for a system according to the present invention.

DETAILED DESCRIPTION OF THE INVENTION

Figure 1:
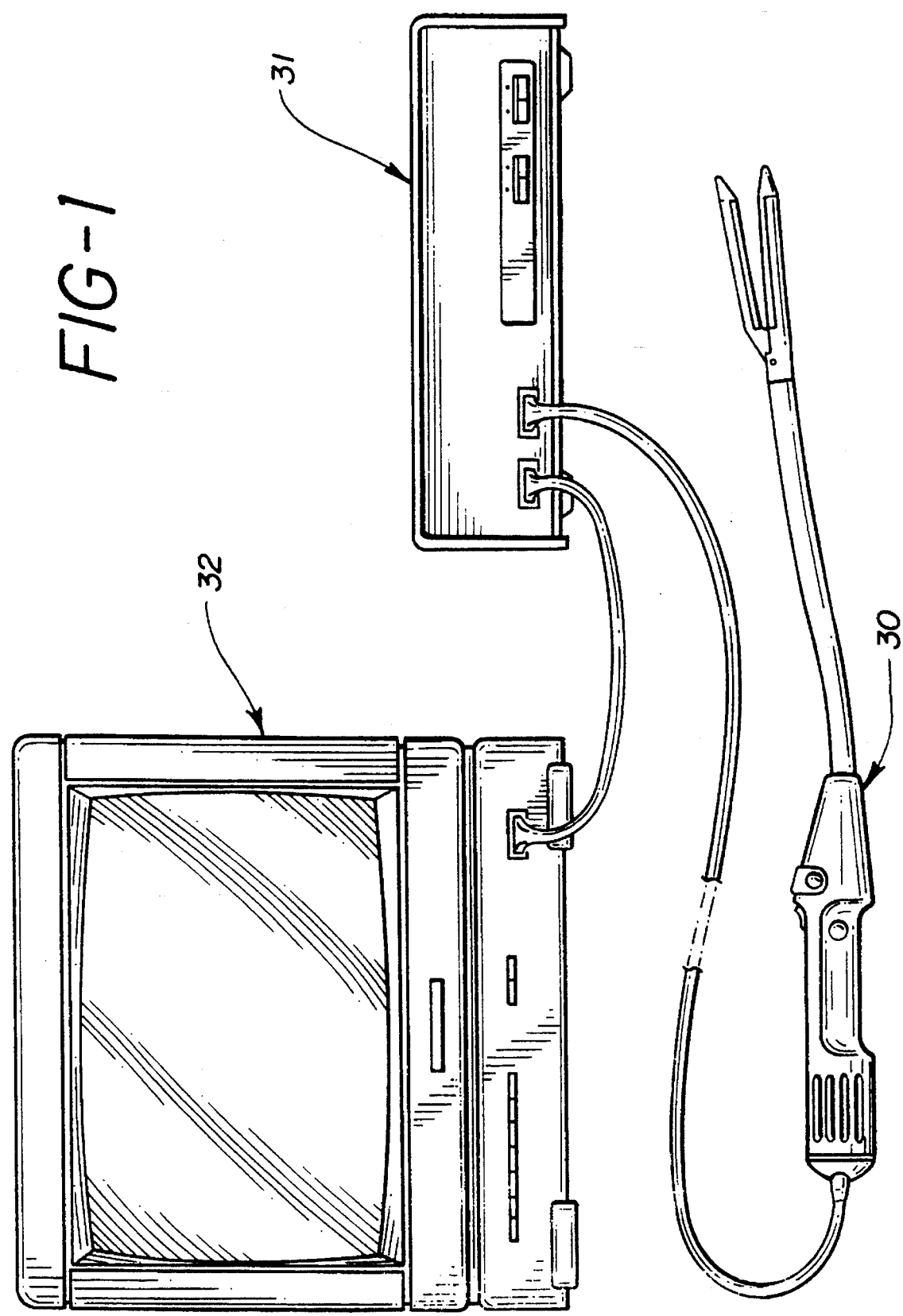
FIG. 1 is a schematic view of an endoscopic surgical system of the present invention interconnected with a microprocessor/controller and a video display screen.

Referring to the drawings, there is shown in FIG. 1 a perspective view of an endoscopic system according to the present invention. In this Figure an endoscopic stapling and cutting instrument 30 is interconnected with a controller 31 and a video display monitor 32. The controller includes a microprocessor, power supply, hard-wired logic, sensor interface and motor drive circuits. The instrument is connected to the controller so that the controller can accept, store, manipulate, and present data. The controller may feed appropriate signals back to the instrument in order to operate the instrument. The controller also acts to supply power to the instrument at the appropriate level, frequency, timing, etc. Within the controller may be several hardwired logic circuits controlling critical instrument functions. Also, several sensing circuits may be incorporated in the controller to measure voltage, current, power etc. The controller may also include a display screen to present the data it has received from the instrument and manipulate it in a desired way.

Figure 2:
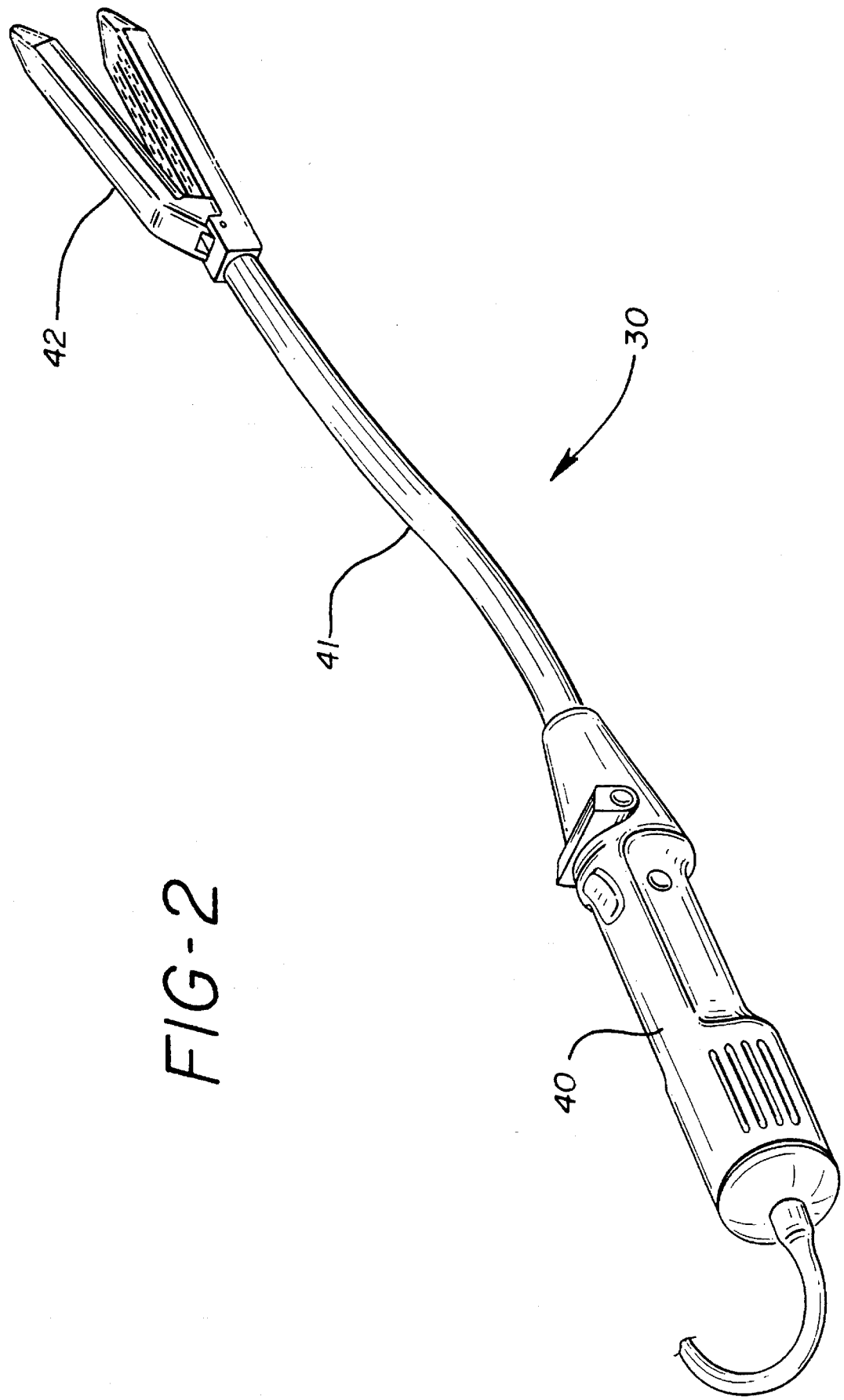
FIG. 2 is a perspective view of an endoscopic stapling and cutting system in accordance with the present invention.

In FIG. 2 there is shown a perspective view of the endoscopic instrument depicted in FIG. 1. The instrument has a handle portion 40. Extending from this handle portion is a shaft portion 41 and at the end of the shaft portion is a desired head or business portion 42 of the instrument. The head or business portion is that portion of the instrument which accomplishes a step in a surgical procedure, whether that be ligating, stapling, cutting, manipulating tissue, or combinations of such steps. The head and shaft portions of the instrument are constructed so that they can be applied through the cannula of a trocar as is well known in endoscopy.

In the embodiment depicted in FIGS. 2 through 9, the head portion is a linear stapler and cutter; that is, the head portion will place down plural parallel rows of staples with the staples offset in the rows. The instrument will also operate a knife to pass between two adjacent parallel rows of staples. Such an instrument staples tissue together and cuts that tissue between the stapled portions. Such instruments are used in various types of surgical procedures such as bowel and lung resections.

FIG. 3 is an enlarged, longitudinal cross-sectional view of the handle portion of the instrument depicted in FIG. 2. In this embodiment, the handle portion includes a small DC motor 45 attached to a gear box 46. Extending from the gear box is a rotatable drive shaft. The rotatable drive shaft extends substantially the length of the handle. Also included in the handle and interconnected with the DC motor are a suitable on-off switch 48 and a switch 49 to control the power supply being provided by the motor. A video display switch may also be provided in the handle if desired. While in this embodiment the motor itself is included in the handle, it should be appreciated that the motor could be separate from the instrument with appropriate connections so that a variety of instruments could be used with detachable motor or power source. Also, if the instrument is to be interconnected with a controller to accept, store and manipulate data, the motor may be connected to such controller and information such as current input, power output, voltage and other parameters may be monitored by the controller for manipulation, display, and use in a suitable manner.

As depicted in the cross-sectional views in FIGS. 4, 4a and 4b, the motor shaft 50 extends into the center of the gear box 46. The gear box comprises two sets of gears 51 and 52, which reduce the rotation of the shaft 47 with respect to the motor at a ratio of 36:1 or other reduction as desired.

Figure 5:
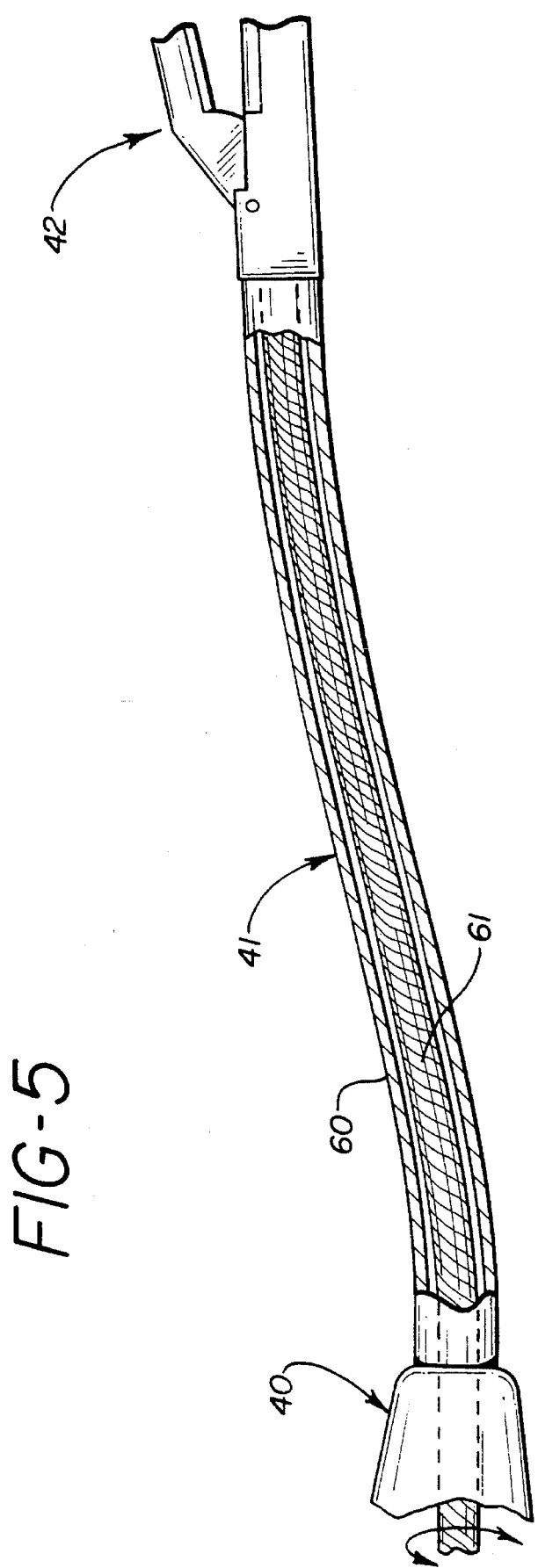
FIG. 5 is a longitudinal cross-sectional view of the shaft of the system depicted in FIG. 2.
Figure 6:
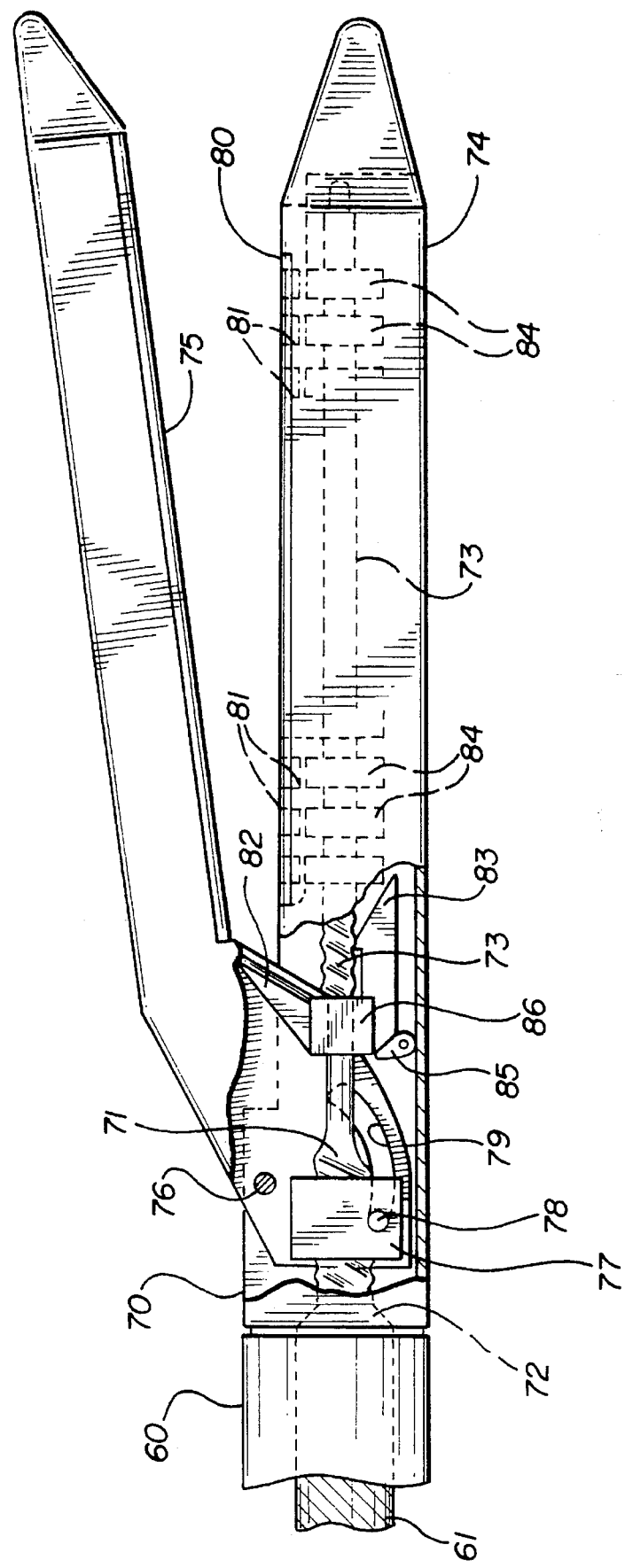
FIG. 6 is an enlarged longitudinal cross-sectional view of the active or business head of the system depicted in FIG. 2.

Referring to FIG. 5, there is shown an enlarged, longitudinal cross-sectional view of the shaft portion of the instrument shown in FIG. 2. In this embodiment, the shaft housing 60 is flexible. Through the center of the housing there extends the rotating, axially flexible, torsionally stiff shaft 61. The housing connects the handle of the instrument to the head of the instrument and the flexible shaft is connected to the drive shaft 47.

FIGS. 6 through 10 are enlarged, longitudinal cross-sectional views of the head portion of the instrument depicted in FIG. 2. The views depict the head of the instrument in the open position prior to being placed on tissue (FIG. 6), in the closed position ready for firing (FIG. 7), during the firing action (FIG. 8), after the firing action has been completed (FIG. 9) and in the final open position (FIG. 10) when the instrument may be removed. In these figures, like parts are identified with the same numerals. The housing 70 of the head is suitably connected to the shaft housing 60 either by a press fit or ultrasonic welding or other similar means. Extending substantially the length of the head and connected to the rotating shaft 61 is a threaded rod 71. The threaded rod has a larger diameter portion 72 adjacent the shaft 61 and a smaller diameter portion 73 for the remainder of the threaded rod. The head includes a staple or staple cartridge portion 74 and an anvil portion 75. The staple portion and the anvil portion are pivotally connected to each other by the anvil pivot pin 76. Mounted on the larger diameter portion of the threaded rod is a closure nut and extending from that closure nut 77 is a closure pin 78 which moves in a slot 79 disposed in the pivotally mounted anvil portion of the head. When the flexible shaft is rotated, the threaded rod is also rotated and on rotating the closure nut will move down the threaded rod and move the closure pin in the closure slot to close the anvil portion against the staple portion of the head of the instrument. Tissue to be treated or manipulated is placed between the anvil portion and the staple portion of the head of the instrument when in the open position. Power is applied to the flexible shaft to rotate the shaft and the threaded rod and close the anvil portion. As can be appreciated, the amount of torque required to pivot the anvil portion about the pivot pin can be sensed and the thickness of tissue between the anvil and the staple portion determined. It is a simple matter for a controller to manipulate this information and inform the surgeon as to whether or not he has the appropriate amount of tissue between the anvil portion and the staple portion of the head of the instrument upon closure or whether he has too much or too little tissue and should re-manipulate the instrument. For a constant voltage drive, the force required to close the instrument may be measured by monitoring motor current. The power delivered to the instrument may be controlled by varying motor voltage and/or current to achieve a constant motor speed with varying load.

Mounted in the staple holding portion of the instrument is a removable staple cartridge 80. The cartridge holds four rows of staples 81. The rows are parallel and in adjacent rows the staples are off-set as is well known in the art. The cartridge is placed so that it is opposite the anvil portion of the instrument and snaps into the staple holding portion of the instrument as shown. As depicted in the figures, extending the length of the staple portion of the instrument is the smaller diameter portion of the threaded rod. Mounted on this rod, to move along the rod as the rod rotates, is a knife member 82 and a driving wedge member 83 which are inner-connected. The wedge member precedes the knife member as they move along the threaded rod. As the wedge member moves down the threaded rod, it drives the staples out of the cartridge, via the individual staple drivers 84. The staples pass through the tissue and against the anvil to form the staples in the tissue. The knife 82 following the driving wedge cuts the tissue between adjacent rows of staples. The driving wedge is actually two pieces; that is, it has one wedge piece on one side of the knife to drive the staples on that side of the knife and a like wedge piece on the opposite side of the knife to drive the staples on that side of the knife.

When the anvil portion 75 is closed as shown in FIG. 7, the closure nut 77 moves a stop member 85 forward so that the firing nut 86 on which the knife 82 and wedges 83 are disposed is moved forward and engages the threads of the smaller diameter portion 73 of the threaded rod to move forward along the rod and drive the staples 81 and cut tissue. The firing nut 86 is biased, using a suitable means, so as not to engage the threaded rod until a stop member 85 is activated. Once the firing nut has moved to its most forward position to drive and form all of the staples and cut the tissue, it engages a suitable contact 87 which immediately reverses the motor to retract the firing nut. In its fully retracted position, the firing nut 86 moves the stop member 85 rearwardly causing the closure nut 77 to then retract and open the anvil portion 75 of the head of the instrument. Another configuration would be to locate contacts in the handle portion of the instrument and use a follower nut on the rotating shaft to monitor position. It should be pointed out that it is desirable to locate as many as possible of the contacts and sensors in the handle portion of the instrument so that the head or business end can be maintained as small as possible and still accomplish the desired step in a procedure. By maintaining the head and shaft of the instrument as small as possible, the opening in the patient required for inserting the instrument may be kept small, thus increasing some of the benefits of an endoscopic procedure. As can be appreciated, various information may be transmitted during the operation of the instrument; for example, the movement of the stop member pushing the firing nut to the threaded rod for movement can be sensed. The most forward position of the wedges and knife may be sensed. The reversal of the motor may also be sensed as well as the movement of the stop member to open the anvil portion etc. Furthermore, if desired the presence of a cartridge and the presence of staples in that cartridge may also be sensed. All of this information may be fed back to a controller and stored and manipulated in the control unit so that the surgeon using the instrument will instantaneously receive information as to the placement of the staples, the cutting of the tissue, the presence of staples in the cartridge, etc.

Referring to FIGS. 11 through 16, there is depicted an endoscopic ligating system of the present invention. The ligator comprises a handle portion 80 having appropriate on-off 81 and power control 82 switches. A hollow circular casing 83 extends from the handle portion and a clip applying head portion 84 is disposed at the opposite end of the circular casing. As more clearly shown in FIG. 12, in the handle portion is a rotatable drive shaft 85. One end of the drive shaft at the rear of the handle includes a connection 86 so that it can be connected to a DC motor or other suitable power means. The opposite end of the drive shaft is threaded 87. The threaded portion of the drive shaft engages a threaded end 88 of a longitudinally moveable rod 89. The rod is connected to longitudinally extending shaft 90. The shaft extends substantially the full length of the instrument from the handle to the head or business end of the instrument. When the drive shaft 87 is rotated, the rod 89 and longitudinally extending shaft 90 move forward and when the rotation of the drive shaft is reversed, the rod and longitudinal extending shaft is retracted.

Figure 13:
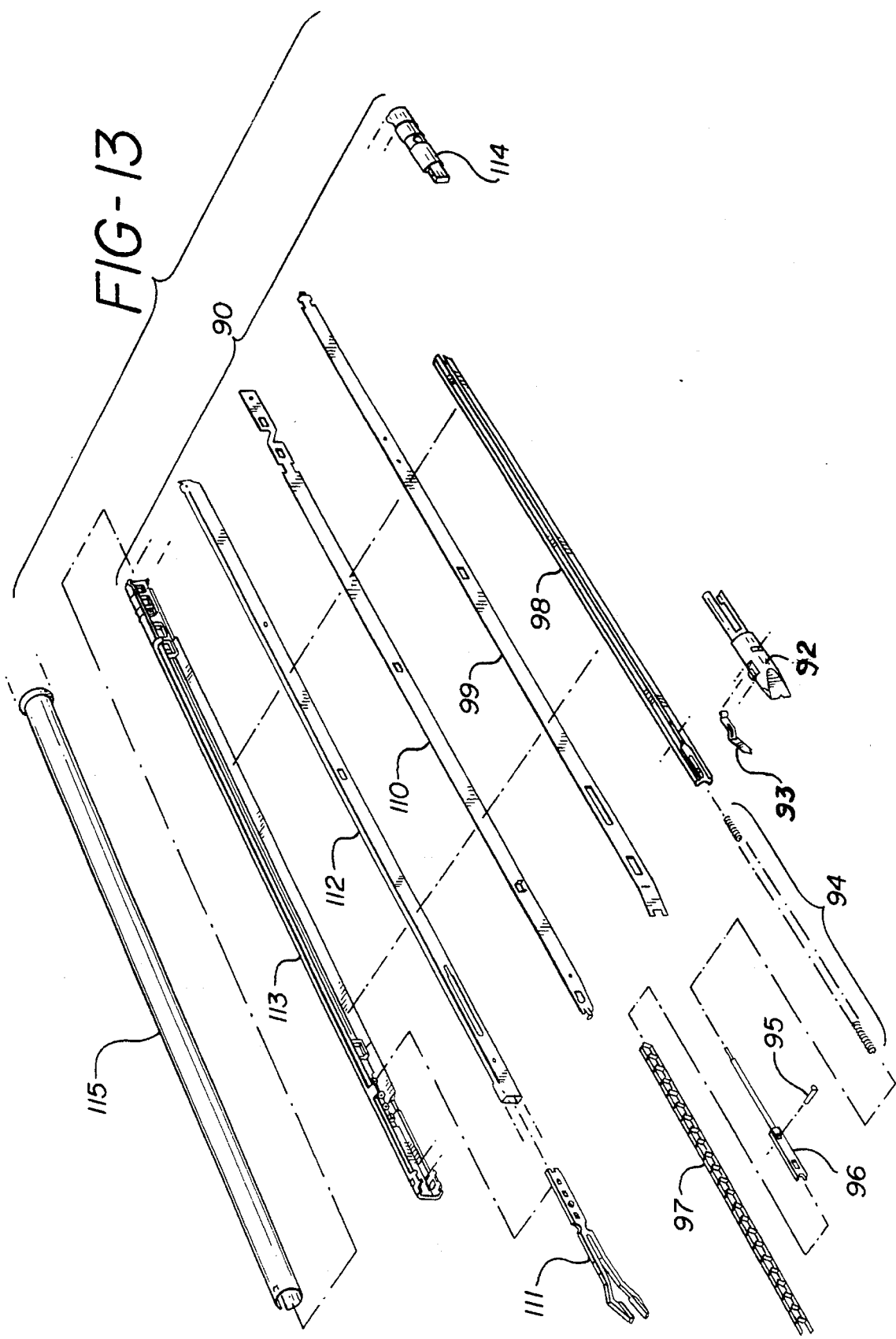
FIG. 13 is an assembly view of the shaft portion of the system depicted in FIG. 11.
Figure 14:
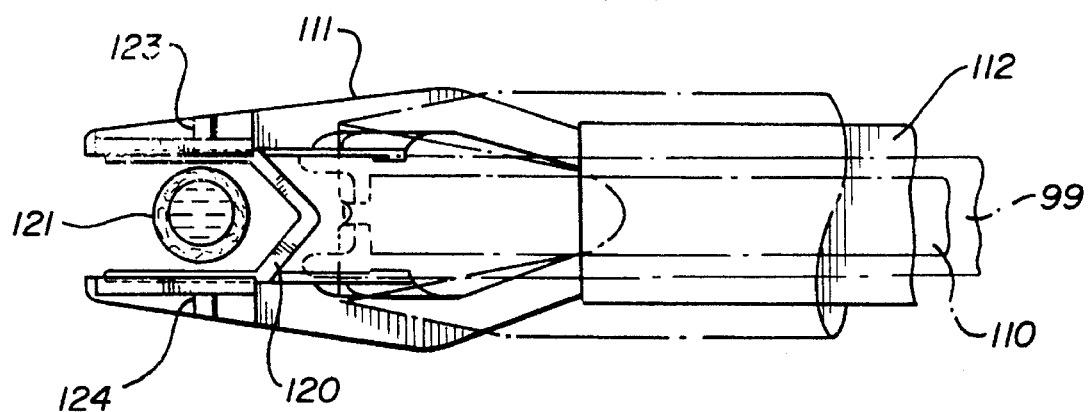
FIGS. 14, 15 and 16 are sequential plan view of a clip placed in the head of the system depicted in FIG. 11 when the clips are open, closing and fully closed, respectively.
Figure 15:
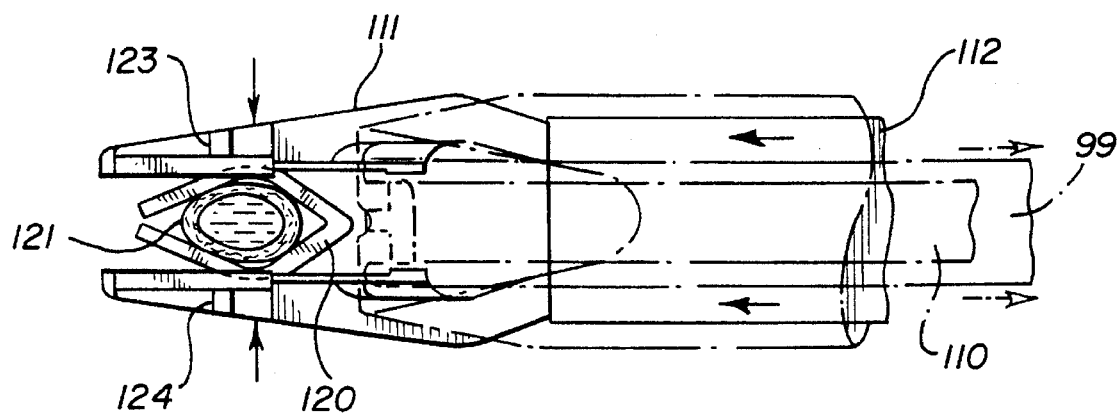
Figure 16:
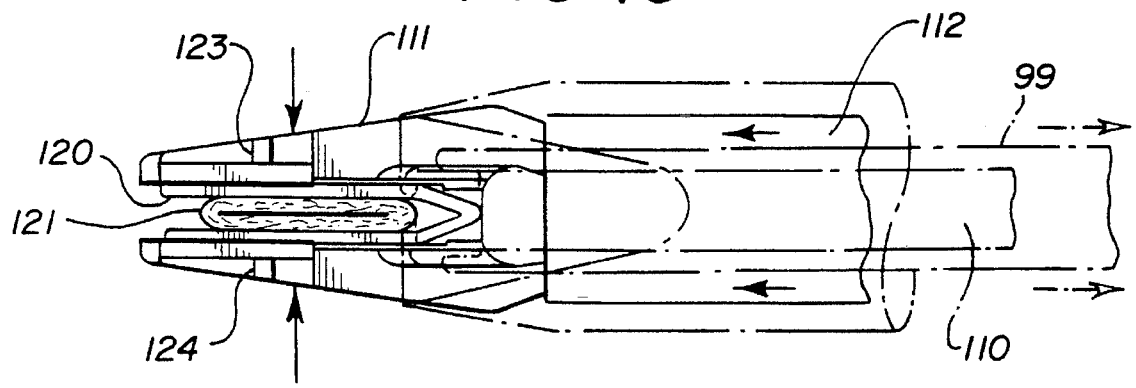

As shown in FIG. 13, the longitudinally extending shaft is mounted in a suitable support tube 115. The shaft comprises a longitudinally moveable cam channel 112, an enclosing member 113, a floor 110 opposite the enclosing member, a feed bar 99, an end cap 114, and a track 98 for holding ligating clips. Attached within the cam channel are the jaws 111 of the instrument. In operation, when the cam channel is moved forwardly, it encloses the jaws and brings them together to close a clip which has been placed in the jaws. When the drive shaft 87 is reversed, the channel retracts and the jaws opens. Also included in the shaft are a magazine or a stack of clips 97 held in track 98. The track also holds a feeder spring 94, lock lever 95 and feed shoe 96. The clips are positioned in the path of the feed bar 99 by spring 94. A lifter spring 93 is held in place over clip track 98 by shroud 92 and acts to place the first clip of the magazine into the plane of the feed bar for position in the jaws. The operation of this portion of the instrument can best be seen in FIGS. 14, 15, and 16. As the cam channel 112 is urged forwardly, it engages the outer surface of the jaws 111 and pushes them towards each other to close the clip 120 about tissue 121. When the cam channel retracts, the jaws open. The clip magazine 97 is advanced forwardly and another clip is placed within the jaws. This happens when the spring 94 is released and the feed shoe advances the next clip from the stack of clips, which has been positioned in the path of the feed shoe by the spring so that another clip may be placed. Suitable sensing members 123 and 124 in the jaws can determine whether or not there is an appropriate clip in the jaws, whether or not the clip is appropriately closed and when the stack of clips is empty. All of this information may be fed back to a controller for storage and manipulation and appropriate information reported to the operator of the instrument.

While I have described my new system with specific reference to a linear stapler-cutter instrument and a ligating clip applier, it of course, can be used with other endoscopic instruments. For example, my new system could be used to control an electro-cauterizing instrument. My new system could be used to control the activation of such an instrument as well as the irrigation and suction used with cauterizing instruments.

In all of the previous embodiments, the sensing mechanism has been used to sense the operation of the instrument and to sense whether or not appropriate tissue is in the appropriate position, etc. It should be appreciated that the instruments may also be designed to sense physical parameters of the surrounding environment. For example, they may sense the blood oxygen content or tissue density of adjacent tissue or various hemostasis characteristics of adjacent tissue and the like may be used.

Figure 17:
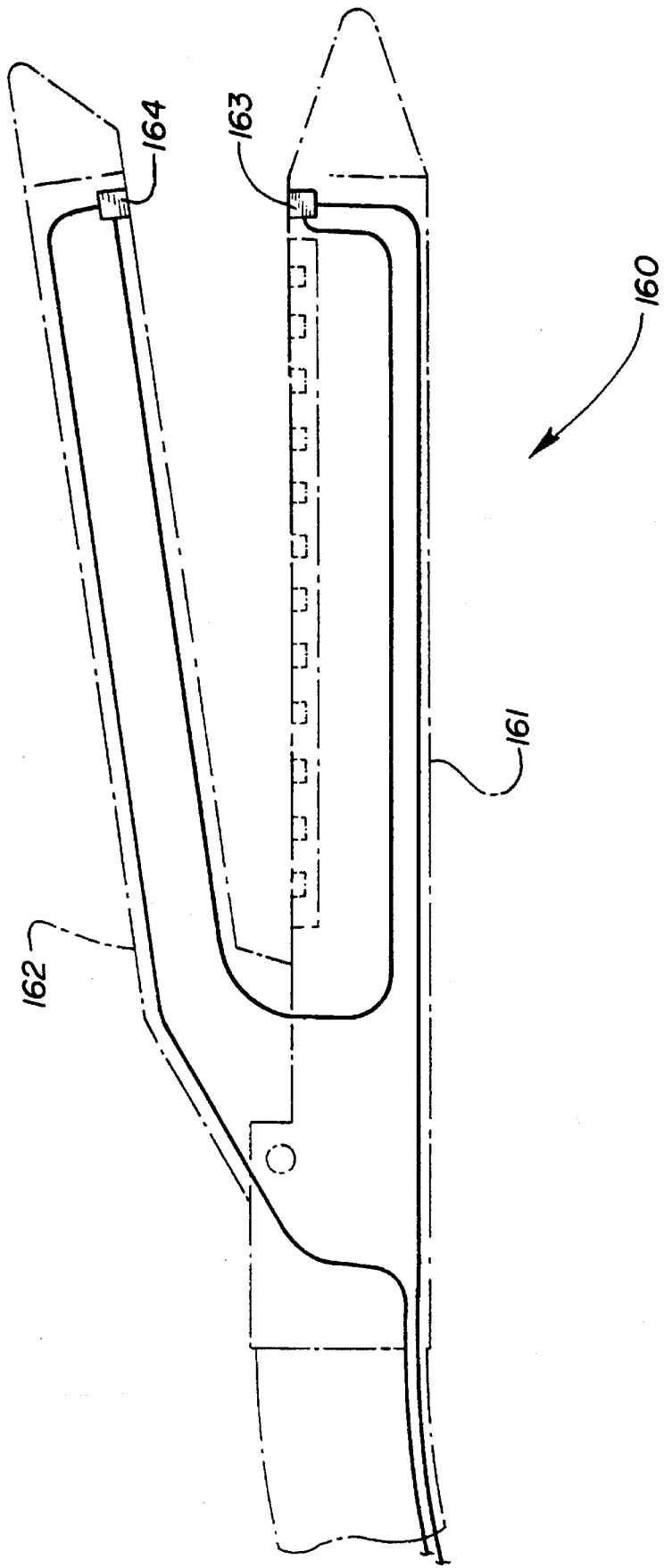
FIG. 17 is a longitudinal cross-sectional view of a head of a system of the present invention depicting sensing means for sensing properties in the surrounding environment.

In FIG. 17, there is depicted the head of an instrument which includes a sensing member used to sense the blood oxygen content of adjacent tissue. In this embodiment, the instrument is a linear stapling instrument though other instruments are also meant to be encompassed in this embodiment. FIG. 17 depicts the head or business end 160 of such an instrument. The head comprises a staple or staple cartridge holding member 161 and a pivotally mounted anvil member 162 similar to that depicted and described in conjunction with FIG. 6. A light emitting diode (LED) 163 and phototransistor receiver 164 are disposed in the staple holding member. The transistor receiver comprises one or more photo-transistors and appropriate resistors. When tissue to be manipulated is placed between the staple member and the anvil member an electrical pulse is applied to the LED to cause light to be emitted by the LED. The emitted light contacts the tissue and, depending on the properties of the tissue, a portion of the light is reflected from the tissue to the photo-transistor thereby creating an electrical signal in direct proportion to the received optical signal. The amount of light striking the photo-transistor may be measured and correlated to a desired property of the tissue such as oxygen content. The indirect measurement of tissue penetration via an opto-electronic signal conversion is used to control desired operations of the instrument. The operations that might be controlled would be the opening and closing of the anvil member and/or the firing of the staples. This is accomplished by feeding the light measurement to a controller which would in turn control the power source used to operate the instrument. Also, this information could be supplied to the surgeon via a video display. The surgeon could use this information to determine proper positioning of the instrument or other procedure related manipulations.

Figure 18:
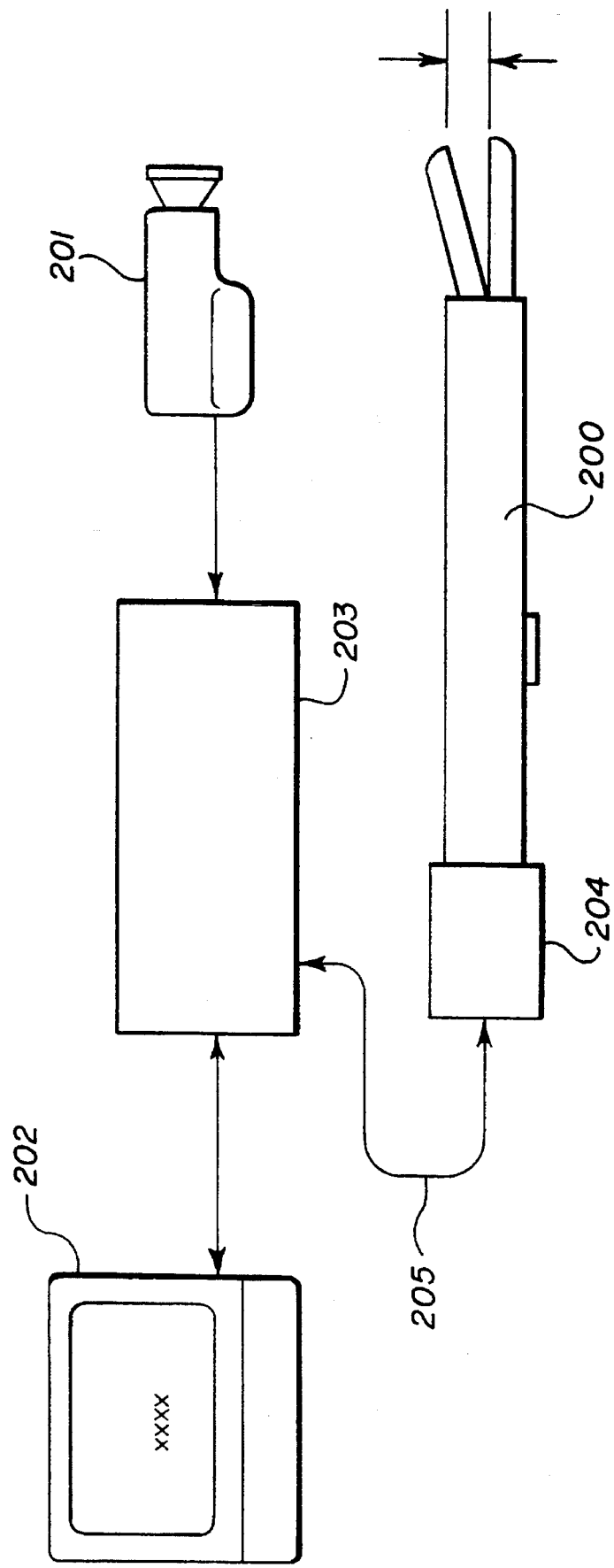
FIG. 18 is a block diagram showing the interrelationship of the principal components of one embodiment of a system according to the present invention.

FIG. 18 portrays in a simple block diagram one form of a system according to the present invention. In this embodiment the endoscopic instrument is a stapler and cutter 200. The status of the instrument and various messages are communicated to the user by an interface with an endoscopic video camera 201 and monitor system 202. The system also includes an instrument microprocessor/controller 203. The endoscopic instrument is powered by a DC motor 204 and is connected to the controller by a cable 205. The controller is micro-processor based and includes circuits for sensing, motor control, sensor interface, video interface and power supply. The instrument includes miniature sensors to detect the power and/or force being used and limit switches and contacts to turn the motor on and off at predetermined positions. Limit switches are also used to detect various interlocks used in the instrument. The instrument may also include sensors to determine the position of the anvil to the cartridge and whether or not staples are present in the cartridge. All sensors, switches, and motors are connected to the controller via the interface cable 205. This information, fed into the appropriate controller, is stored and manipulated and fed to a central processing communication system. Some information will be processed directly through the hard wired circuits. It is important to note that it is desirable to incorporate critical instrument functions in to the hardwired logic of the controller whenever possible. The controller then may be used for non-critical functions and information processing. The processed and manipulated information is fed to a video display screen and/or a suitable written or audio display mechanism. The information may also be fed back to the instrument controller to control some or all of the instrument functions.

Figure 19:
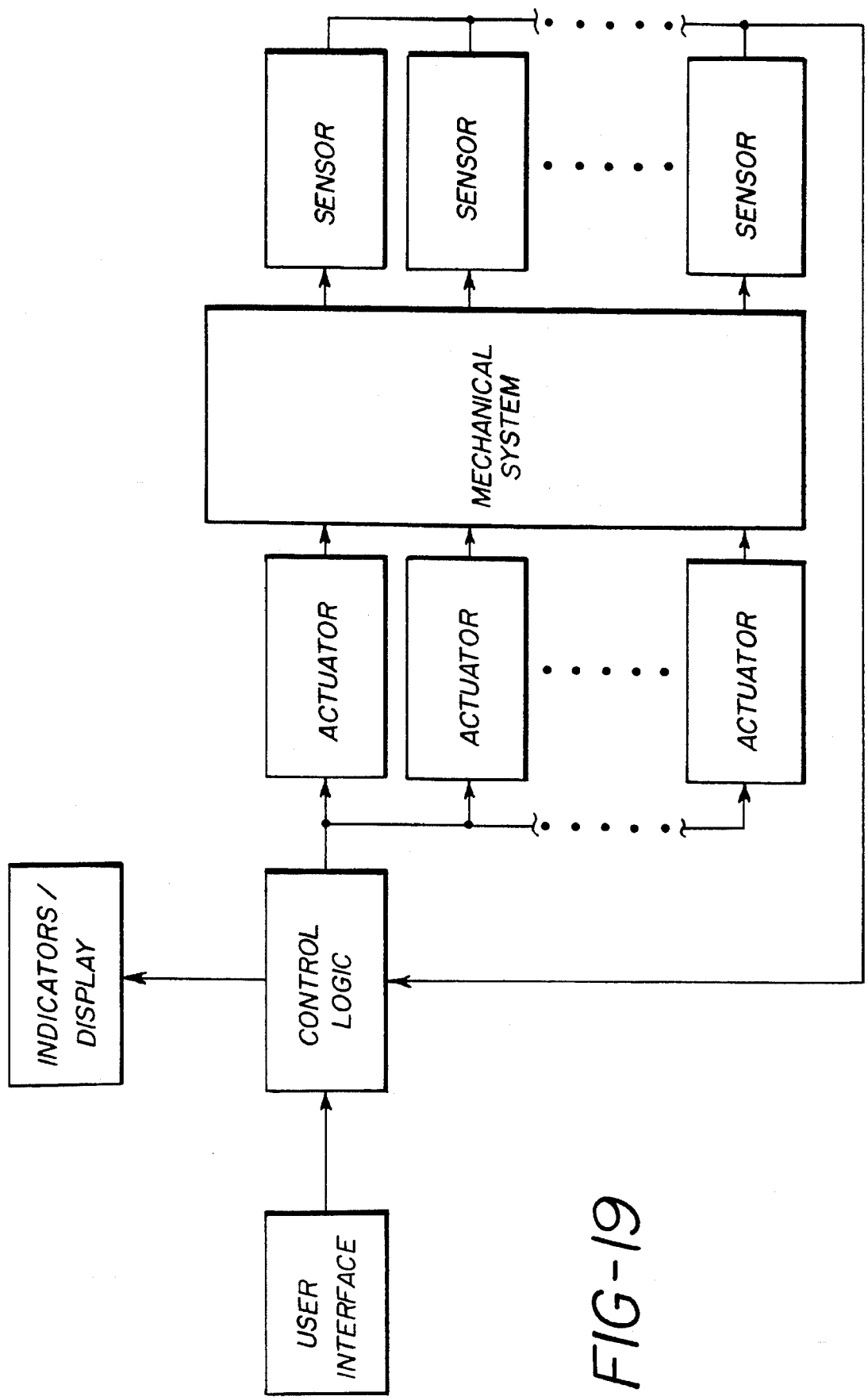
FIG. 19 is a block diagram depicting a possible set of hardware architecture for a system of the present invention.

In FIG. 19 there is depicted a configuration of hardware that could be used in the system of the present invention. From the sensor input from the specific endoscopic instrument used, the control logic can make decisions and/or actions on things such as tissue compression, position and proximity, electrical properties, chemical properties, temperature etc.

The control logic may be based on analog computing, gate array logic, hard-wired combinational logic, or sequential embedded microprocessor control, etc. or even some combination of electrical, mechanical, hydraulic or pneumatic logic.

Figure 20A:
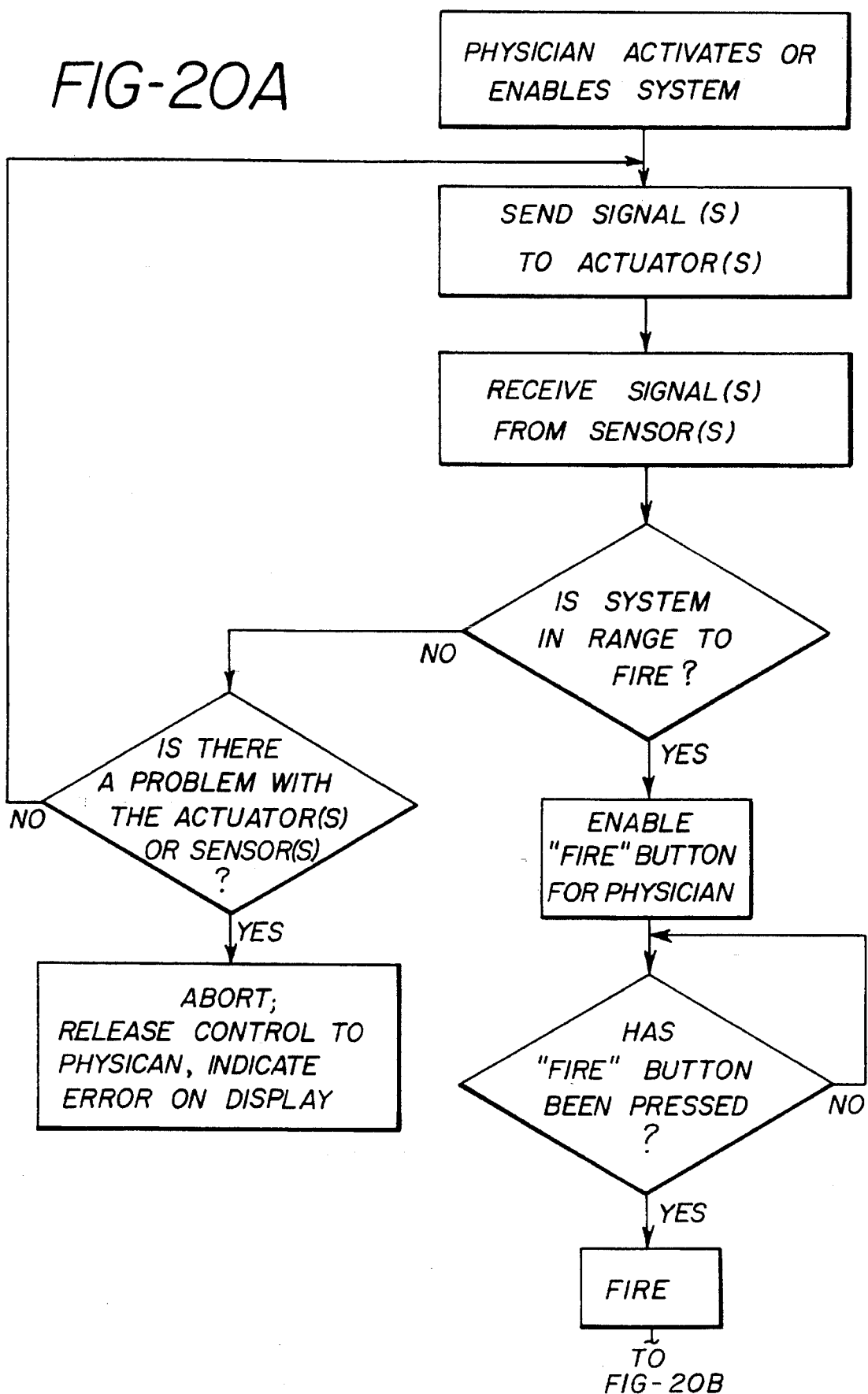

FIG. 20 is a simplified flow diagram for the control logic set forth above and described in conjunction with FIGS. 18 and 19.

It should now be evident that there has been described herein an improved endoscopic system that embodies a high degree of control and reliability while expanding the scope of the actions that can be accomplished by any specific instrument to provide improved endoscopic procedures.

Although the invention has been described by way of examples of preferred embodiments, it will be evident that other adaptations and modifications may be employed without departing from the spirit and scope of the invention.

What is claimed is:

1. A stapling instrument for use in an endoscopic procedure comprising:

a head portion, a handle portion and a connecting portion connecting said head portion to said handle portion;

said head portion comprising means for holding a cartridge of staples, firing means for ejecting staples from said cartridge and anvil means to form said staples, said anvil means being disposed in relationship to said cartridge holding means to allow tissue to be disposed between said cartridge and said anvil means;

a rotatable shaft disposed in said connecting portion;

converting means disposed at one end of said rotatable shaft and connecting said firing means to said shaft to convert the motion of the shaft into a force to eject said staples from the cartridge and form said staples in the tissue, means disposed at the other end of said rotatable shaft for rotating said shaft, a first sensing means disposed in said head portion for detecting a physical property of the tissue placed between said cartridge and said anvil means, a second sensing means for detecting the force used to eject and form the staples; and control means interconnected to both said first and second sensing means to control the ejection and formation of the staples.

2. A stapling instrument according to claim 1 wherein the anvil means is pivotally connected to the means for holding a cartridge of staples at one end thereof.

3. A stapling instrument according to claim 1 wherein the cartridge of staples contains at least 2 parallel rows of staples.

4. A stapling instrument according to claim 3 wherein the head portion includes cutting means reciprocally movable between 2 rows of staples.

5. A stapling instrument according to claim 1 which includes a third sensing means disposed in said instrument for measuring a physical property of the instrument.

6. A stapling instrument according to claim 1 wherein the anvil means is pivotally connected to the means for holding a cartridge of staples at one end thereof, the cartridge of staples contains at lest two parallel rows of staples, the head portion includes cutting means, said cutting means comprising a knife which is movable between adjacent rows of staples and the converting means also converts the motion of the shaft into a force to move said knife.

7. A stapling instrument according to claim 6 which includes a third sensing means disposed in said instrument for determining the position of the knife.

8. A stapling instrument according to claim 1 wherein the firing means is a D.C. motor.

9. A stapling instrument according to claim 8 wherein the D.C. motor is releasably attached to the instrument.

* * * * *